A

(12) United States Patent
Zhang et al.

(10) Patent No.: US 8,092,787 B2
(45) Date of Patent: *Jan. 10, 2012

(54) PERSONAL PRODUCT COMPOSITIONS COMPRISING STRUCTURED BENEFIT AGENT PREMIX OR DELIVERY VEHICLE AND PROVIDING ENHANCED EFFECT OF OPTICAL MODIFIER SEPARATE FROM STRUCTURED BENEFIT AGENT

(75) Inventors: Xiaodong Zhang, Livingston, NJ (US); John R. Glynn, Jr., Westfield, NJ (US); Stephen M. O'Connor, New York, NY (US); Pravin Shah, Rutherford, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 489 days.

This patent is subject to a terminal disclaimer.

(21) Appl. No.: 10/443,396

(22) Filed: May 22, 2003

(65) Prior Publication Data

US 2004/0234470 A1 Nov. 25, 2004

(51) Int. Cl.
- *A61K 8/00* (2006.01)
- *A61K 8/18* (2006.01)
- *A61K 31/33* (2006.01)
- *A61Q 5/00* (2006.01)
- *A61Q 9/00* (2006.01)
- *A01N 43/00* (2006.01)

(52) U.S. Cl. .................................. 424/70.1; 514/183

(58) Field of Classification Search .................. 424/70.1
See application file for complete search history.

(56) References Cited

U.S. PATENT DOCUMENTS

| | | | | |
|---|---|---|---|---|
| 3,211,619 | A * | 10/1965 | Buchwalter et al. | 424/64 |
| 5,653,970 | A * | 8/1997 | Vermeer | 424/70.24 |
| 5,661,189 | A | 8/1997 | Grieveson et al. | |
| 5,674,511 | A * | 10/1997 | Kacher et al. | 424/401 |
| 5,804,540 | A * | 9/1998 | Tsaur et al. | 510/135 |
| 5,817,609 | A | 10/1998 | He et al. | |
| 5,919,815 | A * | 7/1999 | Bradley et al. | 514/449 |
| 5,981,464 | A * | 11/1999 | He et al. | 510/451 |
| 6,080,707 | A * | 6/2000 | Glenn et al. | 510/130 |
| 6,312,678 | B1 * | 11/2001 | Elliott et al. | 424/70.22 |
| 6,338,840 | B1 | 1/2002 | Allan et al. | |
| 6,458,751 | B1 | 10/2002 | Abbas et al. | |
| 6,491,935 | B1 * | 12/2002 | Bekele | 424/401 |
| 6,645,511 | B2 | 11/2003 | Aronson et al. | |
| 6,669,763 | B1 * | 12/2003 | Ghodoussi | 106/10 |
| 6,673,755 | B2 * | 1/2004 | Wei et al. | 510/130 |
| 6,716,440 | B2 | 4/2004 | Aronson et al. | |
| 6,759,376 | B2 * | 7/2004 | Zhang et al. | 510/130 |
| 6,797,683 | B2 * | 9/2004 | Shana'a et al. | 510/370 |
| 2003/0049282 | A1 | 3/2003 | Aronson et al. | |
| 2003/0054019 | A1 | 3/2003 | Aronson et al. | |
| 2003/0082222 | A1 * | 5/2003 | Miyamoto | 424/401 |
| 2003/0157159 | A1 * | 8/2003 | Franklin et al. | 424/450 |
| 2003/0171231 | A1 | 9/2003 | Shana'a et al. | |
| 2003/0199404 | A1 | 10/2003 | Lorenzi et al. | |

FOREIGN PATENT DOCUMENTS

| | | |
|---|---|---|
| WO | 96/02224 A1 | 2/1996 |
| WO | 03/074020 A1 | 9/2003 |

OTHER PUBLICATIONS

Burke et al. Inhibition of pancreatic cancer growth by the dietary isoprenoids farnesol and geraniol. Lipids. 1007;32(2):151-6, abstract only.*
Vamvakas et al. Irinotecan (CPT-11) in combination with infusional 5-fluorouracil and leucovorin (de Gramont regimen) as first-line treatment in patients with advanced colorectal cancer: a multicenter phase II study. Am J Clin Oncol. Feb. 2002. 25(1)65-70, abstract only.*
CAS Registry Information for 145544-09-8 retrieved from STN search results, Apr. 21, 2010.*
The chemistry of petroleum and its substitutes: a practical handbook. By Charles Kenneth Tinkler and Frederick Challenger. New York: D. Appleton and Company, MCMXV. p. 70.*
English translation of Opposition statement filed by opponent against EP 1486195 (10 pages).
English translation of Document D11—Comparative tests with the "W/O Sun-protection Cream with Cetiol CC, SPF 30" formulation of document D1 (3 pages).
Kosmetikjahrbuch (cosmetics yearbook) 2001, pp. 368, formulation W/O Sun-protection Cream with Cetiol CC, SPF 30, Verlag fur die chemische Industrie, Augsburg 2001.
Kosmetikjahrbuch 2002, pp. 142-143, Daily Light Lotion, SPF 15, and non-greasy, water-resistant and preservative-free Sunscreen PF 33. Verlag fur die chemische Industrie, Augsburg 2002.
G.A. Nowak, Die kosmetischen Praparate, Rezeptur, Hersteilung und wissenschaftliche Grundlagen (Cosmetic preparation, formulation, manufacture and scientific fundamentals), $2^{nd}$ edition, p. 642, Verlag fur die chemische Industrie, Augsburg 1975, general knowledge.
Andreas Domsch, Die kosmetischen Praparate, Lipdhaltige und emulgierte Formulierungen (Cosmetic preparations, lipid-containing and emulsified formulations), $4^{th}$ edition, pp. 9, 27-28, 57 and 253, Verlag fur die chemische Industrie, Augsburg 1994. general knowledge.
Cosmetic and Toiletry Formulations, Second Edition, vol. 2, p. 315, formulation Pigmented Cover Crème, Noyes Publications, 1992.
Cosmetic and Toiletry Formulations, Second Edition, vol. 4, p. 76, formulation Liquid Make-Up, Noyes Publications, 1995.
W. Raab, U. Kindl, Pflegekosmetik—Ein Leittaden (skin-care cosmetics—a guide) p. 99, chapter 9.1 Emulsionen, Grundlagen (emulsions, fundamentals*). Wissenschafliche Veriagsgesellschaft, Stuttgart. 1999, general knowledge.
W. Umbach, Kosmetik, Entwicklung, Herstellung und Anwendung kosmetischer Mittel (development, manufacture and use of cosmetic products), $2^{nd}$ edition, pp. 122-125, Georg Thieme Verlag, Stuttgart, 1995, general knowledge.

(Continued)

*Primary Examiner* — Fereydoun G Sajjadi
*Assistant Examiner* — Audrea Buckley
(74) *Attorney, Agent, or Firm* — Ronald A. Koatz

(57) ABSTRACT

The present invention relates to compositions comprising a structured benefit agent pre-mix or delivery vehicle comprising benefit agent structured with crystalline materials, as defined, which when separately prepared and combined after preparation, provides enhanced delivery of optical modifier carried on, trapped within or in the presence of the structured benefit agent.

7 Claims, 4 Drawing Sheets

OTHER PUBLICATIONS

W.J. Schmidt, Polarisationsoptische Versuche mit Bienenwachs (optical polarization experiments with beeswax), Koiloid Zeitschrift, Vo. 100. No. 1 (1942), pp. 140-151.

H.P. Fiedler, Lexikon der Hilfsstoffe fur Pharmazie, Kosmetik und angrenzende Gebiete (dictionary of auxiliary agents for use in pharmacy, cosmetics and related fields), keyword Sonnenblumenol (sunflower oil), Edition Cantor Verlag Aulendorf, 1996, general knowledge.

Pages 5-8 of our response to Opponent's Statement in the Opposition, Jul. 7, 2009.

\* cited by examiner

PERSONAL PRODUCT COMPOSITIONS COMPRISING STRUCTURED BENEFIT AGENT PREMIX OR DELIVERY VEHICLE AND PROVIDING ENHANCED EFFECT OF OPTICAL MODIFIER SEPARATE FROM STRUCTURED BENEFIT AGENT

FIELD OF THE INVENTION

The present invention comprises a structured premix or "delivery vehicle" composition (structured hydrophobic benefit agent(s)) designed to enhance the effect of separate optical modifiers delivered from the same personal product compositions (e.g., liquid soap, bar soaps, creams, emulsions, non-wovens etc.). Specifically, the optical modifier(s) may be entrapped within a network formed by the structured benefit agent (e.g., delivered by the structured benefit agent) or the presence of the structured benefit agent in the final composition may simply enhance activity of the separate optical modifier. When the structured benefit agent composition is separately prepared and combined with the personal product composition (preferably while the structured, premix composition is still in a molten or liquid state), a personal product composition containing the structured benefit agent provides enhanced delivery of the benefit agent(s) and, at the same time, allows separate optical modifier to have an enhanced effect resulting in changes in the visual appearance of skin.

The separate optical modifier(s) may be incorporated into the structured benefit agent delivery vehicle or may be added separately from the premix to deliver enhanced visual appearance, e.g., shine on the skin.

BACKGROUND

Optical modifiers can provide benefits in visual appearance to the skin or hair. At present, however, it is extremely difficult to achieve high levels of deposition and/or to enhance the effects of optical modifiers when delivered from personal product compositions, including but not limited to personal wash liquid cleansers and personal product bars.

While this and co-pending applications are described with personal product language, to the extent the structured benefit agents can be used in a variety of compositions where deposition by benefit agents is desirable (e.g., hair, deodorant), the claims are intended to be read expansively and limited only by structuring component.

Specifically, applicants have found that the use of "structured" benefit agents (the structured benefit agent compositions are separate from the optical modifier) help to enhance the effect of the optical modifiers. The structured benefit agent may carry or entrap the optical modifier(s) or the modifier may have been added separately rather than in a premix used to form the structured benefit agent. In the presence of the structured benefit agent, the separate optical modifier displays an enhanced visual appearance (e.g., shine) compared to the effect of the same optical modifier delivered in formulations where structured benefit agent is not used. According to the invention, preferably the benefit agent being structured and structuring material (e.g., crystalline wax, hydrogenated oil or fat) are separate components.

Specifically, the invention relates to use of benefit agents structured by particular crystalline structurant or structurants (i.e., so that the crystals have specifically defined aspect ratios) wherein, when structured benefit agent is separately prepared before combining with personal product composition, it provides enhanced properties to separate optical modifiers (carried on/within the structured benefit agent or added separately). Enhanced properties may be the result of enhanced deposition of the "structured" benefit agent or other mechanism but this is not critical to the invention.

Unlike prior art references where deposition is dependent on the large size of the benefit agent droplets (e.g., >50 micrometers), the deposition results of the subject invention have no requirement of large droplet size and are not dependent in size.

Among the structurants which may be used to structure the carrying benefit agent are natural or synthetic crystalline waxes. Among natural waxes are included petroleum derived waxes such as paraffins and microcrystalline waxes; as well as animal and plant (vegetable) waxes. Among the synthetic crystalline waxes which may be used are crystalline polymers such as polyethylene. Structurants may further include natural or synthetic hydrogenated oils or fats, fatty acids, fatty alcohols, salts of fatty acids, hydroxy fatty acids and fatty acid esters.

When the structured benefit agent(s) carries/entraps optical modifiers (or structured benefit agents are present in final formulation even if modifiers are added separate from premix), visual changes in skin appearance are achievable. Particles having a wide range of shapes, surface characteristics, and hardness characteristics can be utilized to provide the optical effect of these optical modifiers. The water-insoluble particles of the present invention can be derived from a wide variety of materials including those derived from inorganic, organic, natural, and synthetic sources.

Some prior art references purport to use rheological parameters to select oils or oil blends to be used for improving deposition or providing favorable sensory feel.

U.S. Pat. No. 5,674,511 to Kacher et al., for example, describes the use of solubility parameters and four rheological parameters to select benefit agents (i.e., oil or oil blends) that can be used in moisturizing cleansing formulations to improve deposition and provide favorable sensory feels. Petrolatum and petrolatum-containing mixtures are said to be favorable selections. The reference fails to teach or suggest the building of a deformable network of crystals within the benefit agent, and which crystals must have a specific aspect ratio. The Kacher reference fails to teach or suggest that the structured benefit agent be combined with other components in the compositions in a molten, semi-molten or solid state. Also, it does not describe separate benefit agent and structurant, as is preferred by the subject invention (i.e., in the subject invention, if petrolatum is used, it is preferably used as a structurant to structure other benefit agents rather than itself comprise the structured benefit agent). In short, the benefit agents (e.g., oils) of Kacher clearly do not appear to be internally structured delivery vehicles like those used in the compositions of the invention which are separately prepared and wherein structurant has defined aspect ratio.

A number of prior art references disclose generally the concept of an oil additive which can thicken or stabilize oils. They do not, however teach or disclose that specific crystalline structurant (i.e., having a defined aspect ratio), when prepared in combination with a benefit agent as a premix/delivery vehicle will enhance properties of a separate optical modifier which is carried or entrapped by the structured benefit agent or which optical modifier is found in the final formulation with the structured benefit agent.

U.S. Pat. No. 5,804,540 to Tsaur et al. and U.S. Pat. No. 5,661,189 to Grieveson, for example, disclose use of both crystalline or micro-crystalline waxes and hydrophobic polymers to thicken low viscosity oil so as to control the oil droplet size (i.e., it must attain a certain minimum size to deposit) as well as to maintain high lather. As noted above, however, there is no discussion of the criticality of crystalline structure (aspect ratio) or that a thickened benefit agent must be separately prepared and added in a molten, semi-molten or solid state. Further, as noted, there is no recognition that it is critical the thickener must be a specific natural or synthetic crystalline structuring material (as defined in the subject invention).

In copending U.S. patent application Ser. No. 09/859,862 to Aronson et al. (entitled "Wet-Skin Treatment Composition"), filed May 17, 2001 and Ser. No. 09/859,849 to Aronson et al. (entitled "Method of Enhanced Moisture or Reduced Drying Using Wet-Skin Treatment Compositions"), there is disclosed benefit agents which provide a draggy feel. There is no teaching or disclosure, however, of using benefit agent structured with crystalline materials of specific aspect ratio (and carrying, containing or in the presence of optical modifiers) or of how to produce such.

No prior art of which applicants are aware demonstrates the use of natural or synthetic crystalline structurants (e.g., wax), having specific aspect ratio of crystals and prepared as a premix, to enhance the properties of optical modifiers (through the enhanced deposition of the structured benefit agent carrying the modifier or through other mechanism).

BRIEF DESCRIPTION OF THE INVENTION

Accordingly, the present invention relates to personal product compositions (including liquid soap, creams, emulsions, non-wovens, bars), comprising structured benefit agent composition for delivering enhanced benefit of optical modifiers. Liquid compositions of the invention comprise:

(1) 0-99%, preferably 1 to 75%, more preferably 3 to 70% by wt. surfactant (2) 0.1 to 90% by wt. of a benefit agent delivery vehicle wherein:
  (a) 0.1 to 99.9, preferably 0.5 to 99.5, more preferably 1 to 99% by wt. of the structured delivery vehicle comprises one or more benefit agents or mixtures; and
  (b) 99.9 to 0.1%, preferably 99.5 to 0.5% by wt. of the structured delivery vehicle comprises a crystalline structurant or structurants selected from the group consisting of natural and synthetic waxes, natural or synthetic hydrogenated oils or fats, fatty acids, fatty alcohols, salts of fatty acids, hydroxy fatty acids, fatty acid esters, and mixtures thereof;

(3) optical modifier or modifiers,
  wherein crystals of the crystalline structurant (e.g. wax) have an aspect or axial ratio such that length A to width B of the crystals has a ratio A/B>1, The length is to be understood as the longer of the two dimensions when considering both length and width.

Bar compositions of the invention comprise:

(1) 1 to 80%, preferably 3 to 65% by wt. surfactant; and (2) 0.1 to 90% by wt. of a benefit agent delivery vehicle (structured benefit agent) wherein:
  (a) 0.1 to 99%, preferably 0.5 to 99.5, more preferably 1 to 99% by wt. of the structured delivery vehicle comprising one or more benefit agents or mixtures thereof; and
  (b) 99.9 to 0.1%, preferably 99.5 to 0.5% by wt. of the structured delivery vehicle comprises a crystalline structurant or structurants selected from the group consisting of natural and synthetic waxes, natural or synthetic oils or fats, fatty acids, fatty alcohols, salts of fatty acids, hydroxy fatty acids, fatty acid esters and mixtures thereof;

(3) optical modifier or modifiers,
  wherein crystals of the crystalline structurant (e.g. wax) have an aspect or axial ratio such that length A to width B of the crystals has a ratio A/B>1, The length is to be understood as the longer of the two dimensions when considering both length and width.

When said premix (structured benefit agent composition) is separately prepared and separately combined with a final carrying composition (i.e., surfactant containing or non-surfactant containing personal product composition), in which the structured benefit agent will be used, said final composition will provide enhanced visual appearance effect (e.g., enhanced effect of greater than about 5%) of optical modifiers carried on or entrapped within the structured premix or found separately in the final formulation because added separate from premix. Optical modifiers which may be used to provide optical effects can be particles having a wide range of shapes, surface characteristics, and hardness characteristics. The water-insoluble particles of the present invention can be derived from a wide variety of materials including those derived from inorganic, organic, natural, and synthetic sources.

The structured benefit agent premix should preferably pour sufficiently so that it can be added to the carrying composition which is why, generally, it will be in molten or semi-molten state. However, it can also be added in a solid state. The deposition of the benefit agent in the structured benefit agent is not dependent on large droplet size of the structured benefit agent (i.e., can be small or large drops).

The use of structured benefit agent also enhances delivery of separate benefit agents in the premix (which may or may not be structured) and of separate benefit agents added separately form the premix.

As noted, the structured benefit agent or delivery vehicle of this invention may be used in bar or non-bar (preferably liquid), personal product compositions. The composition will typically comprise (a) 0 to 99%, preferably 1 to 75% of a surfactant system comprising a surfactant or surfactants selected from the group consisting of anionic, nonionic, amphoteric/zwitterionic, cationic surfactants and mixtures thereof and (b) 0.1 to 90%, preferably 0.5 to 80%, even more preferably 1-40% by weight of the structured benefit agent delivery vehicle as defined above.

In one embodiment of the invention, the invention comprises a process for forming non-bar, preferably liquid, personal product composition comprising the structured benefit agent delivery vehicle noted above which process comprises:

(1) mixing benefit agent carrier (which may or may not carry the separate optical modifier) and crystalline structurant, preferably although not necessarily, at a processing conditions (e.g., a temperature sufficiently high) so that a premix of the benefit agent and structurant will be flowable and will pour (e.g., having viscosity of less than 250 Pa-s, more preferably less than 200 Pa-s, most preferably less than 100 Pa-s);

(2) combining said separately prepared premix and the carrying composition (which contains the optical modifier if not enhanced in the premix), preferably with stirring;

(3) if necessary, because the mixture had been heated, cooling the resulting mixture to room temperature.

In another aspect of the invention, the invention comprises a process for forming a personal cleansing bar product composition comprising the delivery vehicle noted above which process comprises:

(1) mixing hydrophobic benefit agent or agents (which may also carry the separate optical modifier) and crystalline structurant at a temperature above the melting point of the structurant and then either cooling to ambient temperature so that it can be combined later with the bar carrying composition, or optionally cooling to the temperature at which the carrying composition is mixed before combining with the carrying composition;

(2) combining said separately prepared premix and the carrying composition (which contains the separate optical modifier if not contained in the premix), preferably with stirring or mixing at elevated temperature;

and then either (3) pouring the resulting mixture into molds and cooling (actively or passively) to room temperature;

or (4) cooling the resulting mixture to flakes (e.g., by passing the resulting mixture over a chill roll), taking the flakes (e.g., from the chill roll) and extruding the material into a billet which is then formed or stamped.

In another embodiment, the invention provides a method for providing enhanced visual shine of at least 5 intensity units which method comprises applying a personal product cleanser comprising:

(a) 0 to 99%, preferably 1 to 75% by wt. surfactant; and
(b) 0.1 to 90% of benefit agent vehicle comprising:
  (i) 0.1 to 99.9% by wt. structured benefit agent vehicle comprising one or more benefit agents;
  (ii) 99.9 to 0.1% by wt. of structured benefit agent vehicle comprising a crystalline structurant wherein the structurant is selected as noted above; and
(c) optical modifier or modifiers.

Optical modifiers generally may comprise about 0.1 to 3% by wt., preferably 0.2 to 2.5% by wt., more preferably 0.5 to 2% by wt. of the cleanser.

DETAILED DESCRIPTION OF THE INVENTION

The present invention relates to a personal product composition comprising a structured benefit agent delivery vehicle composition which, because of the structure of the crystal used to prepare it (for example, aspect ratio of the crystalline structurants), and, because of its manner of preparation (separately prepared), forms a structured benefit agent component which, when optionally cooled, has particular properties (e.g., yield stress, shear thinning). The structured benefit agent not only permits the benefit agent which is structured to deposit more efficiently from the composition, but also permits enhanced visual appearance (e.g., shine) by optical modifiers carried on or in the structured benefit agent or outside the premix but in the presence of the structured benefit agent in the final composition.

Figure 1:
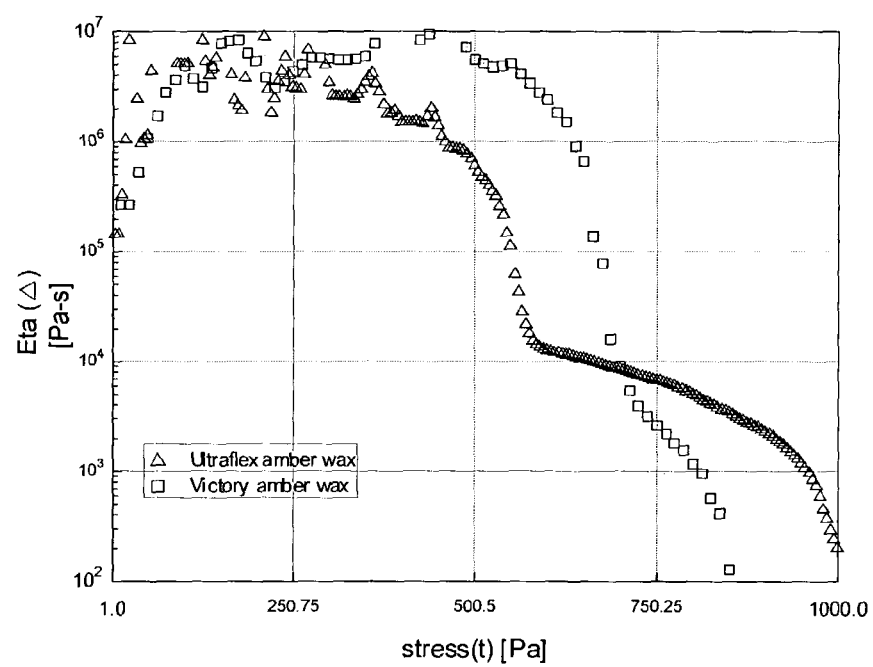
FIG. 1 is a yield stress plot of a structured benefit agent composition comprising sunflower seed oil structured with a wax (Ultraflex amber or Victory amber) of the invention. Ultraflex amber wax and Victory amber wax were each mixed with sunflower seed oil at a ratio of wax/oil of 1:4. The graph shows how the structured benefit agent yields under high stress, a property specific to the structured benefit agents of the invention. At low stresses the viscosity of the structured benefit agent composition, (measured in Pascal seconds, or Pa-s) is essentially constant. As the applied stress is increased and reaches the yield stress value, the viscosity drops sharply and the material flows more readily.
Figure 2:
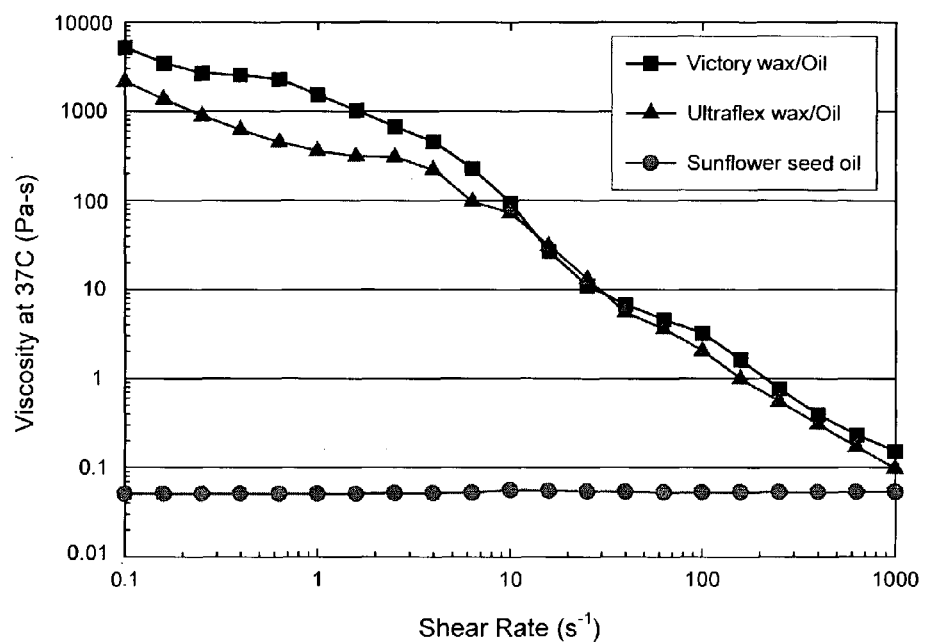
FIG. 2 is a plot showing shear thinning behavior of structured benefit agents of the invention versus an unstructured benefit agent. Ultraflex amber wax and Victory amber wax were each mixed with sunflower seed oil at a ratio of wax/oil of 1:4. For comparison, the viscosity behavior with shear of unstructured sunflower seed oil is also shown. Plotted is viscosity versus shear rate. At low shear rates the viscosity of structured benefit agents, sunflower seed oil structured with wax (Ultraflex amber wax or Victory amber wax) is very high. As the applied shear rate is increased the viscosity of the structured benefit agents decreases and continues to decrease at the higher shear rates. At sufficiently high shear rates the viscosity of structured benefit agents approaches that of the pure unstructured benefit agent component.

Yield stress parameters of the structured benefit agent can be 1-5000 Pa or higher and all ranges subsumed therein (see FIG. 1) and shear thinning parameters can range from 2000 Pa-s (or higher) at low shear rates (0.1/sec) (i.e., viscosity of 1000 to 10,000 Pa-s as seen on the Y axis of FIG. 2) to 0.1 Pa-s (or lower) at high shear rates (100/sec) (again, see FIG. 2). Both yield stress and shear-thinning parameters/ranges are dependent on the level of benefit agent structurant added to benefit agent.

When specific crystalline materials are used to structure the benefit agent, and when the process of the invention is used, the final composition containing the structured benefit agent vehicle will deliver the structured benefit agent to the skin or substrate at a level of at least about 5% greater, preferably at least 10% greater than if structured benefit agent is not used. Deposition is not dependent on large droplet size of the structured benefit agent droplets in the carrying composition (e.g., liquid soaps). Because of this enhanced deposition of the structured benefit agent, there is an improvement in the benefit of the optical modifier of at least 5% (e.g., in one embodiment there is shine enhancement of greater than 5 intensity units).

Optical modifiers can be particles having a wide range of shapes, surface characteristics, and hardness characteristics any of which can be utilized to provide optical effect. The water-insoluble particles of the present invention can be derived, for example, from a wide variety of materials including those derived from inorganic, organic, natural, and synthetic sources. Non-limiting examples of these materials include those selected from the group consisting of almond meal, alumina, aluminum In oxide, titanium dioxide, mica, coated mica, sodium stearate, stearic acid, zinc stearate, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like.

The "structured" benefit agent of the subject invention can be envisioned as an emollient droplet which has certain physical properties defined at least in part by the ability of the structured benefit agent to deliver the benefit agent more efficiently from the final composition. The structured benefit agent enhances properties of separate optical modifiers carried by, entrapped in, or in the presence of the structured benefit agent in the final formulation.

More specifically, when structurants structure the benefit agent, the crystals in the benefit agent phase are believed to create a solid network which is apparently interconnected like a "house of cards" for plate-like crystals or perhaps more like a scaffold structure when the crystalline structurant has rod/needle morphology. The crystals form a three-dimensional supporting network that, without wishing to be bound by theory, is believed to make the structured benefit agents more than just thickened benefit agents (see FIG. 4). The crystalline structure changes the normally fluid benefit agent (e.g., vegetable or other oils) into solid-like materials that have good flow and spreading properties for benefit agent deposition. Through selection of structurant (e.g., wax) and calculation of structurant content, the structured benefit agent can be tailored to meet desired rheological parameters. An important part of the invention is that the crystal forming this 3-D network must have an aspect or axial ratio of length and width (A and B, respectively) such that $A/B > 1$. This aspect ratio of the crystals is believed to enhance deposition of the structured benefit agent (see FIG. 3). The length is to be understood as the longer of the two dimensions when considering both length and width.

The structured benefit agents of the invention have been found to deposit much more effectively than if the benefit agent is not structured. Moreover, they enhance visual appearance benefits from separate optical modifiers.

The structured benefit agent can be seen as a premix since it is a critical aspect of the invention that the benefit agent being structured and the crystalline structurant forming the "structure" be combined before adding to the carrying composition in which the structured benefit agent will be used. In this sense, the premix or structured benefit agent is acting as a vehicle for delivery of the benefit agent.

Further, the structured benefit agent may also enhance properties of separate optical modifiers either by carrying or entrapping these benefit agents in a network formed by the structured benefit agent, and also when another benefit agent is separately added to the premix.

The structured benefit agent vehicle thus specifically comprises:
(a) 0.1 to 99.5%, preferably 0.5 to 99.5% by wt. (including all ranges subsumed therein) of the vehicle comprising one or more benefit agents or mixtures thereof; and
(b) 99.9 to 0.1, preferably 99.5 to 0.5% by wt. (including all ranges subsumed therein) of the vehicle comprising crystalline structurant selected from the group consisting of natural and synthetic wax, natural or synthetic hydrogenated oils or fats, fatty acids, fatty alcohols, salts of fatty acids, hydroxy fatty acids, fatty acid ester or mixtures thereof.

The benefit agent may also optionally comprise optical modifiers although there may be added separately outside the premix forming the structured benefit agent and be present only in the final formulation with the structured benefit agent.

Optical Modifiers

The optical modifiers (carried or within the structured benefit agent carriers or in their presence in final formulation) may be single or mixture of two or more modifiers. Because of enhanced deposition of structured benefit agent, there is an improvement of the benefit provided of at least 5% greater than if no structured benefit agent is used. For example, some optical modifiers may provide shine enhancement of at least 5, preferably at least 10 intensity units.

A preferred list of optical modifier includes: particles having a wide range of shapes, surface characteristics, and hardness characteristics can be utilized to provide optical effect. The water-insoluble particles of the present invention can be derived from a wide variety of materials including those derived from inorganic, organic, natural, and synthetic sources. Non-limiting examples of these materials include those selected from the group consisting of almond meal, alumina, aluminum oxide, titanium dioxide, mica, coated mica, sodium stearate, stearic acid, zinc stearate, aluminum silicate, apricot seed powder, aftapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like.

Structured Benefit Agent Carriers

This section refers to benefit agents which are structured and act as carrier carrying or entrapping optical modifiers. As noted, structured benefit agents also used to enhance properties of the optical modifiers even if those modifiers were added outside the premix but are in the presence of the structured benefit agent in the final formulation.

The structured benefit agent of the subject invention may be a single benefit agent component. Further the benefit agent may be a mixture of two or more components, one or all of which may have a beneficial aspect.

The benefit agents can be emollients, moisturizers, anti-aging agents, anti-inflammatory agents, skin-toning agents, skin lightening agents, sun screens, fragrances, etc.

The preferred list of benefit agents include:

(a) silicone oils, gums and modifications thereof such as linear and cyclic polydimethylsiloxanes; amino, alkyl alkylaryl and aryl silicone oils;

(b) fats and oils including natural fats and oils such as jojoba, soybean, sunflower seed oil, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, petrolatum, vaseline, microcrystalline wax, ceresin, squalene, pristan, paraffin wax and mineral oil;

(f) higher fatty acids such as behenic, oleic, linoleic, linolenic, lanolic, isostearic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) octocrylene(2-ethylhexyl 2-cyano-3,3-diphenylacrylate), octyl salicylate (2 ethylhexyl salicylate), benzophenone-3 (2-hydroxy-4-methoxy benzophenone), and avobenzone (4-tert-butyl-4'-methoxydibenzoylmethane) (these are merely illustrative);

(m) phospholipids;

(n) anti-aging, wrinkle-reducing, skin whitening, anti-acne, and sebum reduction agents such as alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives and (o) mixtures of the foregoing.

Although not listed above, hydrophilic benefit agents may also be entrapped in the structured benefit agent network of the premix or separately added outside the premix. This is discussed, for example, in applicants' copending application relating to hydrophilic benefit agents hereby incorporated by reference into the subject application.

Natural or Synthetic Crystalline Structurant

The crystalline structurant used for "structuring" the benefit agent oil or emollient carrier of the subject invention may be a natural or synthetic crystalline wax. Mineral, animal or plant (vegetable) waxes are all described as natural waxes. Synthetic waxes are described as those waxes that have been synthetically polymerized from raw materials or chemically modified natural waxes.

Among the natural crystalline waxes which may be used are petroleum based waxes such as paraffins and microcrystalline wax. Chemically, both microcrystalline (MC) and paraffin waxes are very similar, consisting of long saturated hydrocarbon chains. Both types of waxes are separated from crude petroleum with the MC waxes typically having higher molecular weights. Paraffin wax is extracted from the high boiling fractions of crude petroleum during the refining process by cooling and filtering. Following a sweating process to remove remaining oil in the wax, the resulting paraffin wax typically has less than 0.5% oil. There are many different grades available mostly varying in melting point. Generally, paraffin waxes are colorless or white and transparent. Paraffin waxes consist mainly of straight chain molecules with a small amount of branched-chain molecules having branching near the end of the chains. As a result of the long, straight chains, paraffin wax has large, well-formed crystals. Molecular weights of paraffin waxes generally range from 360 to 420 (26 to 30 carbon atoms), although versions with longer chains (molecular weights up to 600) are available. Typical melting points are 126-134° F. (52-57° C.), the high molecular weight versions have melting points near 170° F. (77° C.). Paraffin waxes are brittle and the addition of oil weakens the structure (lowers the tensile strength).

Microcrystalline waxes (MC) differ from paraffin waxes in physical properties, chain structure and length, crystal type and in the process of manufacture. They are tougher, more flexible and have higher tensile strength and melting points than paraffin waxes. MC waxes have high affinity for oil which, when added, increases the wax plasticity. MC wax cannot be distilled without decomposition and therefore is separated from the residual distillation fraction of crude petroleum by dewaxing processes involving recrystallization in organic solvents and centrifugation. Oil content varies with grade but is usually around 2 to 12%. MC waxes contain mostly branched-chain molecules located at random along the chain with some straight chains. Typical melting points are 145 to 195° F. (63-91° C.). The crystals of MC wax are small and irregular and consist of several types: plates, malcrystalline and needle. A high penetration number indicates flexibility of the wax, but flexibility is not a function of melting point.

There are also other mineral waxes such as montan wax, lignite wax, osocerite, ceresin, utah wax and peat wax.

Animal waxes can be obtained from such things as bees, insects or whales, These waxes include but are not limited to beeswax, Chinese wax, shellac wax, spermaceti and wool wax. Beeswax, for example, classified as an animal wax, is secreted by the honey bee to construct the honeycomb. The wax is harvested by melting the honeycomb and filtering away the wax. Natural beeswax is a crystalline solid and is composed of myricyl palmitate, cerotic acid and smaller amounts of hydrocarbons, cholesterol esters and ceryl alcohols. Beeswax has melting points around 61-65° C. and is compatible with almost all waxes and oils.

Plant waxes can be derived from beans, leaves and berries. Plant or vegetable waxes can include bayberry, candelilla, carnauba, cotton, esparto, fir, Japan, ouricury, palm, rice-oil, sugar cane, ucuhuba and cocoa butter.

Among synthetic crystalline waxes which may be used are crystalline polymers such as polyethylene, Fischer-Tropsch waxes such as polymethylene, chemically modified waxes, polymerized alpha olefins and synthetic animal waxes. For example, siliconyl beeswax may be used which is beeswax that has been chemically modified.

A sample of various waxes which may be used according to the subject invention and of their properties is set forth below in Table 1.

TABLE 1

Waxes and their Properties

| Wax | Classification* | Manufacturer | Penetration No.** (25° C.) | Melting Point (° C.) |
|---|---|---|---|---|
| Ultraflex Amber | MC | Bareco Products | 27 | 74.1 |
| Victory Amber | MC | Bareco Products | 28 | 79.1 |
| White Petrolatum | MC | Penreco | — | 54 |
| Multiwax ML-445 | MC | Crompton Corp. | 30 | 79.4 |
| Multiwax 180-M | MC | Crompton Corp. | 18 | 85 |
| Multiwax W-835 | MC | Crompton Corp. | 70 | 76.7 |
| Multiwax X145A | MC | Crompton Corp. | 40 | 74 |
| Paraffin Wax 150/155 | P | Frank B. Ross Co., Inc. | 12 | 67 |
| Siliconyl Beeswax | DN | Koster Kuenen, Inc. | N/A | 70 |
| Be Square 175 white | MC | Bareco Products | 15 | 82.5 |
| Be Square 175 black | MC | Bareco Products | 18 | 82.3 |
| Perrowax 2250F | MC | The International Group | N/A | 40 |
| Beeswax NF | N | Frank B. Ross Co., Inc. | 18 | 62.5 |

MC: microcrystalline;
P: paraffin;
N: natural/animal;
dN: derivative of natural/animal wax
**Penetration No.: Penetration number values as reported by manufacturers using the standard test method for needle penetration of petroleum waxes of the American Society for Testing and Materials (ASTM D1321). The depth of penetration of needle in tenths of a millimeter (dmm) is measured with a penetrometer that applies a standard needle to the sample for 5 seconds under a load of 100 grams.

Another structuring material of the invention (e.g., used for structuring other benefit agents) is the microcrystalline wax petrolatum (also known as petrolatum or mineral jelly), which typically comprises about 90% by wt. of a natural mixture of microcrystalline waxes plus minor amounts of other impurities.

In addition, structurant may be a natural or synthetic hydrogenated oil or fat. Hydrogenated oils are also commonly referred to as fats. Hydrogenated oils and fats are further classified into their animal or vegetable origin. In addition some fatty acids and fatty alcohols can be used as structurant as well as salts of fatty acids, hydroxy fatty acids and fatty acid esters.

Hydrogenated oils are prepared by the catalyst-induced reaction of unsaturated double bonds in the fatty acid chains of the oils with hydrogen. Oils are fully or partially hydrogenated to make them more solid and to improve their stability against oxidation. Hydrogenated oils are wax-like, hard and can be brittle. They are compatible with oils and when mixed with oils at high temperature will cool to form solid masses.

Hydrogenated oils can be hydrogenated vegetable oils, hydrogenated coconut oil, hydrogenated palm kernel oil, hydrogenated rapeseed oil and many others. Another hydrogenated oil is castorwax. Castorwax is prepared from the hydrogenation of castor oil to create a hard, high melting, wax-like material.

It is well known that triglyceride fats have characteristic polymorphic crystals. Of the three polymorphic forms of crystals for triglycerides (alpha, beta prime and beta) the beta prime crystals are the smallest (<1 μm).

Along with size and shape, a high concentration of particles is required so that the crystals interact in the dispersion. Above a certain critical volume fraction of crystals, these interactions will lead to a buildup of a network that extends throughout the whole volume. The crystal network creates a solid-like material having viscoelastic properties.

Thus, the ability of the fat crystals of the hydrogenated oils to form continuous networks that entrap the oil depends on the solid fat content in the fat/oil mixtures and also on crystal morphology. For example, when there is a high concentration of beta prime crystals, a continuous network of small crystals extends through the sample and the sample is solid and stable. Typically, at solid fat contents of 40-50%, the consistency is hard and brittle, at 20-30% the system is solid-like but yielding, at lower concentrations the consistency is more fluid often with a grainy texture and at very low concentrations the fat crystals separate from the liquid. However, the exact concentrations of crystals required to build desired structures varies depending on the fat and oil used. In practice, the crystal formation is also dependent on processing conditions such as temperature, crystal formation rate and shearing.

A sample of various fats and hydrogenated oils that may be used according to the subject invention and their melting point temperature is set forth below in Table 1.

TABLE 1

Properties of Hydrogenated Oils, Fatty Alcohols and Fatty Acids

| Hydrogenated Oil/Fat | Manufacturer | Melting Point (° C.) |
|---|---|---|
| Castorwax | CasChem | 70 |
| Stearine | Loders Croklaan | 60 |
| Alkofine R | Karlshamns | 60 |
| Lipex 408 | Karlshamns | 50 |
| Hydrogenated Palm Kernel Oil | Karlshamns | 35 |
| Hydrogenated coconut oil | Karlshamns | 42 |
| Stearyl alcohol | Aldrich | 54 |
| Stearic acid | Sigma | 53 |

Crystalline long chain fatty acids and long chain fatty alcohols can also be used to structure benefit agents. Examples of fatty acids are myristic acid, palmitic acid, stearic acid, arachidic acid and behenic acid. Examples of fatty alcohols are palmityl alcohol, stearyl alcohol, arachyl alcohol and behenyl alcohol. Some crystalline fatty acid esters and glyceride esters will also provide structuring benefit.

In addition, the crystalline materials can be combined with other structuring materials such as natural and synthetic waxes to form composite networks to structure benefit agents.

Structured Benefit Agent

As noted above, the structurant in the structured benefit agent is believed to form a three-dimensional supporting network which is believed to make the structured benefit agent more than just thickened benefit agents. That is, it changes the consistency of the fluid benefit agent (e.g., oil) to a solid-like material having good spreading/deposition properties. Deposition is believed to occur by transfer of structured benefit agent droplets/particles to the substrate surface from the composition where the crystalline structure of the structuring material crystals (e.g., aspect ratio) is believed to help enhance affinity of the structured benefit agent to the substrate.

Other benefit agents in the premix may also structure (i.e., 2 or more) or just one may structure and/or the other benefit agent may have enhanced deposition by being entrapped in the network formed by the structured benefit agent.

The benefit agent may comprise 0.1 to 99.9% by wt. of the delivery vehicle/premix and structurant may comprise 99.9 to 1% by wt. of the delivery vehicle. Preferably benefit agent is 0.5 to 99.5%, more preferably 1 to 99% of vehicle. In some preferred embodiment, benefit agent comprise 50-99% of vehicle while wax is 1 to 50%, preferably 2 to 45% of benefit agent vehicle.

When used, for example, as part of a cleanser emulsion where structuring material (e.g., wax) is 20% of benefit agent phase, droplet diameters of the structured benefit agent may be in the range of 1-15 µm, with average droplets having a size of 4-8 µm. As noted, however, there is no requirement that droplets must be of this size.

When incorporated into liquid cleanser formulations, the structured benefit agent droplets are generally solid when stored at room temperature and may be seen as particles. The droplets may be somewhat spherical but have a rough, textured surface, a result of the structurant crystal within the drops.

It has also been noted that material with high crystalline structure (e.g., paraffin, microcrystalline wax) yields excellent deposition of benefit agent.

As mentioned earlier, there is no large size requirement for the structured benefit agent droplets of the invention. Unlike prior art, the structured oils can deposit high oil amounts of structured benefit agent even at small droplet sizes, i.e., below 10 µm and possibly even submicron.

As also mentioned, low levels (<50% of benefit agent) of structurant can be used.

Figure 3:
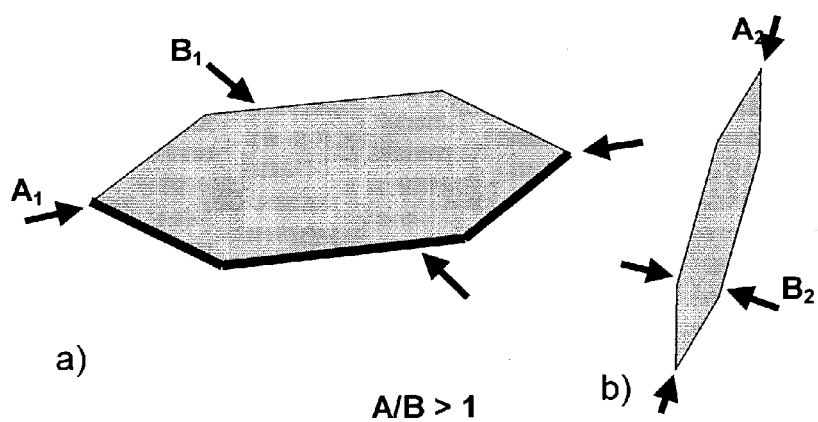
FIGS. 3a and 3b are schematics of typical crystal structurants of the invention having length "A" and width "B". As noted, the aspect or axial ratio of A/B must be greater than 1. The length is to be understood as the longer of the two dimensions when considering length and width.
Figure 4:
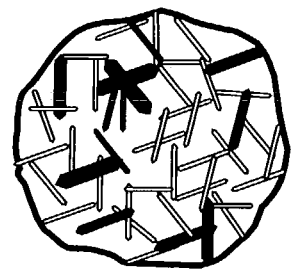
FIG. 4 is a schematic of structurant crystals (which can be "plate-like") forming a three-dimensional network within the structured benefit agent (e.g., oil).

The only criticality is that the shape of the structurant have high axial or aspect ratio (A/NB>1). This is shown in FIG. 3. The length is to be understood as the longer of the two dimensions when considering length and width. The fact that structuring exists is shown by high yield stress observed on benefit agents even when using low amount of structurant (see FIG. 1).

The structured benefit agent of the invention may also be used in combination with other materials that have been shown to enhance the deposition of hydrophobic benefit agents (e.g., cationic polymers, inorganic thickening agents such as clays or silicas, and polymer thickening agents).

Finally, as noted, the structured benefit agent aids in enhancing effect of other non-structured benefit agents which are not part of premix. This phenomenon is described, for example both here (for optical modifiers if not part of premix) as well as other of applicants co-filed, co-pending applications.

Process

A critical aspect of the subject invention is that the benefit agent being structured and crystalline structurant must be combined (e.g., in a premix) before they are combined with the remaining composition. The combination of such premix with carrying composition should be when the structured benefit agent is in a molten, semi-molten or solid state and preferably, although not necessarily, such that it can be poured into the carrying composition. The combination of such premix with carrying composition should preferably, although not necessarily, be when the structured benefit agent is in a molten or semi-molten state such that it can be poured into the carrying composition. That is, the viscosity of structured benefit agent premix when mixing should be no higher than about 250 Pa-s, more preferably 200 Pa-s, most preferable 150 Pa-s.

In one embodiment of the invention, the crystalline structurant and benefit agent are combined and may be heated to a temperature above the melting point of the structurant. These are then preferably mixed to uniformity.

Preferably, the molten material is added to a carrying composition, preferably a surfactant containing carrying composition and maintained at the same temperature as the benefit agent and structurant mixture. After mixing (about 10 seconds to an hour, preferably 5 minutes to 45 minutes), the mixture is cooled, if necessary, to room temperature. As noted, structurant is combined with benefit agent before addition to the carrying composition (e.g., aqueous surfactant phase). It should be noted that a pourable viscosity, if desirably used, may also be obtained by vigorous mixing of structurant and benefit agent and that heating is not necessarily required.

When such process is followed, the resulting structured benefit agent compositions will have the properties described above (i.e. shear thinning, yield stress etc.) and provide in deposition of the structured benefit agent, when measured from the carrying composition, of 5% greater, preferably at least 10% greater relative to level of deposition of benefit agent to substrate from final composition if the benefit agent had not been structured, or the benefit agent not being in the presence of the final formulation of a structured benefit agent. In one embodiment, the carrying composition is liquid and there is resulting deposition of structured benefit agent of at least at least about 60 µg/cm$^2$, preferably at least about 75 µg/cm$^2$, more preferably at least about 100 µg/cm$^2$. In another embodiment, when measured from a bar, resulting deposition of benefit agent is at least about 5 µg/cm$^2$.

Compositions

In one embodiment of the invention, the premix comprising structured benefit agent may be used in a liquid (e.g., personal wash cleanser) composition. Typically, such composition comprises as follows:

(1) 0% to 99%, preferably 1 to 75%, more preferably 3 to 70% by wt. of a surfactant selected from the group consisting of anionic, amphoteric, nonionic and cationic surfactant and mixtures thereof;

(2) 0.1% to 90%, preferably 0.5% to 80% of a delivery vehicle comprising 0.1 to 99.9% delivery vehicle benefit agent or agents containing optical modifiers and 99.9 to 0.1% delivery vehicle crystalline structurant(s) selected from the group consisting of natural and synthetic crystalline waxes, natural or synthetic hydrogenated oils or fats, fatty acids, fatty alcohols, salts of fatty acids, hydroxy fatty acids, fatty acid esters and mixtures thereof;

(3) about 0.1 to 3%, preferably 0.2 to 2.5% by wt. optical modifier or modifiers;

(4) optional ingredients for liquid personal cleanser; and (5) balance water, wherein the premix (structured benefit agent) is delivered to liquid compositions as a separate premix; and wherein deposition of oil/emollient from the liquid composition onto substrate is greater than 5%, preferably greater than 10% relative to deposition of same benefit agents not present in accordance with invention.

In addition, when the structured benefit agent is used, there is an improvement of the benefit provided by the optical modifier of at least 5% than if the structured benefit agent is not used.

For example, in one embodiment, the optical modifier may be present when mixed as part of a premix forming a delivery vehicle (2) above or added outside the premix and use of structured benefit agent may result, in one embodiment where the benefit is shine, in a shine enhancement of at least about 5 intensity units.

In the specific liquid embodiment noted above, oil benefit agents will have deposition onto substrate of greater than 60 µg/cm$^2$.

In another embodiment of the invention, the premix comprising oil/benefit agent may be used in a bar (e.g., personal cleansing bar) composition. Typically, such composition comprises as follows:

(1) 1 to 80%, preferably 3 to 65% by wt. of a surfactant selected from the group consisting of anionic, amphoteric, nonionic and cationic surfactant and mixtures thereof;
(2) 0.1% to 90%, preferably 0.5% to 80% of a delivery vehicle comprising 0.1 to 99.9% delivery vehicle benefit agent or agents and 99.9 to 0.1% delivery vehicle crystalline structurant(s) selected from the group consisting of natural and synthetic crystalline waxes;
(3) 0.1 to 3%, preferably 0.2 to 2.5%, more preferably 0.5 to 2.0% by wt. optical modifier or modifiers;
(4) 0.1 to 80%, preferably 5% to 70% by wt. total composition a structuring aid and/or filler; and
(5) optional ingredients for personal cleansing bar,
wherein the premix (structured benefit agent) is incorporated into bar compositions as a separate premix; and
wherein deposition of oil from the composition onto substrate is greater than 5%, preferably greater than 10% relative to deposition of same benefit agent not prepared in accordance with the invention.

In addition, when the structured benefit agent is used, there is an improvement of the benefit provided by the optical modifier of at least 5% than if the structured benefit agent is not used.

In the specific bar embodiment noted, oil benefit agents will have deposition onto substrate of greater than 5 $\mu g/cm^2$.

Surfactant System (for Liquids & Bars)
Anionic Surfactants

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$-$C_{22}$ alkyl and M is a solubilizing cation;
amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R\text{—}O\text{—}(CH_2CH_2O)_n\overset{O}{\overset{\|}{C}}CH_2CH(SO_3M)CO_2M$$

wherein n=1 to 20; and M is as defined above.

Sarcosinates are generally indicated by the formula RCON($CH_3$)$CH_2CO_2M$, wherein R ranges from $C_8$ to $C_{20}$ alkyl and M is a solubilizing cation.

Taurates are generally identified by formula $$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

Another class of anionics are carboxylates such as follows:

$$R\text{—}(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5-15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application.

Another surfactant which may be used are $C_8$ to $C_{22}$ neutralized fatty acids (soap). Preferably, the soap used are straight chain, saturated $C_{12}$ to $C_{18}$ neutralized fatty acids.

In general the anionic component will comprise from about 1 to 20% by weight of the composition, preferably 2 to 15%, most preferably 5 to 12% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2\text{—}Y^{(+)}\overset{(R^3)_x}{\overset{|}{\text{—}}}CH_2\text{—}R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of Such Surfactants Include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

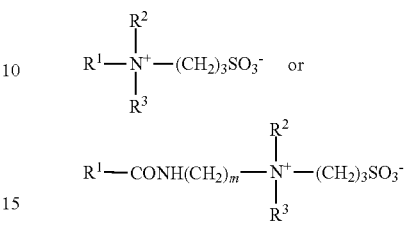

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $—CO_2—$ or $—SO_3—$ Suitable amphoteric detergents within the above general formula include simple betaines of formula:

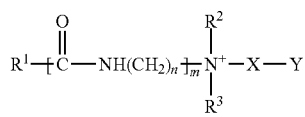

and amido betaines of formula:

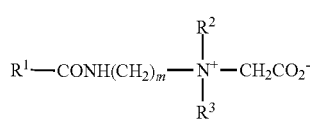

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula $$R^1—\overset{R^2}{\underset{R^3}{N^+}}—(CH_2)_3SO_3^-$$ or $$R^1—CONH(CH_2)_m—\overset{R^2}{\underset{R^3}{N^+}}—(CH_2)_3SO_3^-$$

where m is 2 or 3, or variants of these in which $—(CH_2)_3 SO^-_3$ is replaced by

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 5% to 15% of the composition.

In addition to one or more anionic and optional amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Structurant Benefit Agent Premix

The benefit agent portion of the structured liquid may be any of the benefit agents described previously in the section relating to the benefit agent and additionally comprises optical modifiers.

Similarly, the crystalline structurant may be any one of the materials described above.

The premix/delivery vehicle is also as described above.

As indicated earlier, the premix should be made separately and it can be liquid (molten), semi-molten or solid before adding to final carrying composition. When used in a liquid, the premix may be in pourable or flowable state (viscosity is lower than 250 Pa-s, more preferably lower than 200 Pa-s, most preferably lower than 150 Pa-s) before adding to final carrying composition (e.g. liquid composition).

When using the benefit agent premix of the invention (either structured benefit agent or being in the presence of structured benefit agent, even if added separately from premix, the benefit agent will deposit in an amount at least 5% or greater, preferably at least 10% greater than if no structured benefit agent is present in the final formulation.

Moreover, because of enhanced deposition using structured benefit agent, there will be improved benefit (e.g., shine enhancement, improved matte appearance) of at least about 5% relative to if no structured benefit agent is used.

In one embodiment, when used in a liquid, a benefit agent oil will permit deposition of greater than 60 µg/cm$^2$, preferably greater than about 75 µg/cm$^2$, more preferably greater than 100 µg/cm$^2$ and this deposition is not dependent on large droplet size of the structured benefit agent. Furthermore, in a specific embodiment, such improved deposition results in shine enhancement of greater than about 5 intensity units as measured by shine intensity test described in the protocol section.

In a second embodiment when used in a bar composition, a benefit agent oil will have deposition of greater than 5 µg/cm$^2$ and this deposition is not dependent on large droplet size of the structured benefit agent.

Bar Compositions

Structuring Aids or Fillers

The compositions may also contain 0.1 to 80% by wt., preferably 5 to 70% by wt. of a structurant and/or filler. Such structurants can be used to enhance the bar integrity, improve the processing properties, and enhance desired user sensory profiles.

The structurant is generally long chain, preferably straight and saturated, ($C_8$-$C_{24}$) fatty acid or salt thereof or ester derivative thereof; and/or branched long chain, preferably straight and saturated, ($C_8$-$C_{24}$) alcohol or ether derivatives thereof.

A preferred bar structurant is polyalkylene glycol with molecular weight between 2000 and 20,000, preferably between 3000 and 10,000. Those PEGs are commercially available, such as those marketed under the tradename of CARBOWAX SENTRY PEG8000® or PEG4000® by Union Carbide.

Other ingredients that can be used as structurants or fillers include starches, preferably water soluble starches such as maltodextrin and polyethylene wax or paraffin wax.

Structuring aids can also be selected from water soluble polymers chemically modified with hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® (PEG modified glyceryl cocoate, palmate or tallowate) from Rewo Chemicals.

Other structuring aids which may be used include Amerchol Polymer HM 1500 (Nonoxynyl Hydroethyl Cellulose).

12-Hydroxy stearic acid may be used as a component of the bar structuring system. Such structurant is described, for example in U.S. Pat. No. 6,458,751 to Abbas et al., hereby incorporated by reference into the subject application.

Other Bar Ingredients

In addition, the bar compositions of the invention may include 0 to 15% by wt. optional ingredients as follows:

Perfumes (as described in section on benefit agents); sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers which may be used include Quatrisoft LM-200 Polyquaternium-24, Merquat Plus 3330-Polyquaternium 39; and Jaguar® type cationics.

Polyethylene glycols as conditioners which may be used include:

| Polyox | WSR-205 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

Cationic polymers, like other benefit agents, may be included in the bar surfactant/structurant filler carrying composition or they may be added into the premix benefit delivery vehicle along with the wax.

Typically, bars will also comprise 1 to 30%, preferably 2 to 20% water. The amount of water may vary depending on type of process and structuring material used.

Non Bar Composition Optional Ingredients

The non-bar, preferably liquid compositions of the invention may include optional ingredients as follows:

Another optional element of the invention is an emulsion stabilizer (found in, for example, liquid aqueous phase). The dispersion stabilizer is intended to provide adequate storage stability to the composition (i.e., so the benefit agent delivery vehicle is stable in the composition). The structured composition otherwise may be prone to separate under the action of gravity (creaming or sedimentation depending upon its density). The structured composition of the invention may also be prone to sticking together and coalescing.

The most effective dispersion stabilizers are those that can provide an adequate structure to the liquid, e.g., aqueous phase to immobilize the droplets thus preventing both gravitational separation and collision with other droplets. However, if the dispersion is too stable, the droplets of structured composition are inhibited from coming into proximity with the skin and thus effectively depositing. Therefore, the most effective dispersion stabilizers provided have excellent stability in the container but lose their effectiveness in immobilizing the structured benefit agent when they are applied to wet skin.

Aqueous dispersion stabilizers useful in the instant invention can be organic, inorganic or polymeric stabilizers. Specifically, the compositions comprise 0.1 to 10% by wt. of an organic, inorganic or polymeric stabilizer which should provide physical stability of the large structured oil droplets in the surfactant composition at 40° C. for over four weeks.

Inorganic dispersion stabilizers suitable for the invention include, but are not limited to clays, and silicas. Examples of clays include smectite clay selected from the group consisting of bentonite and hectorite and mixtures thereof. Synthetic hectorite (laponite) clay used in conjunction with an electrolyte salt capable of causing the clay to thicken (alkali and alkaline earth salts such as halides, ammonium salts and sulfates) particularly useful. Bentonite is a colloidal aluminum clay sulfate. Examples of silica include amorphous silica selected from the group consisting of fumed silica and precipitated silica and mixtures thereof.

Organic dispersion stabilizer are defined here as organic molecules that have a molecular weight generally lower than 1000 Daltons and form a network in the aqueous phase that immobilizes the dispersed structured oil phase. This network is comprised either of amorphous solids, crystals, or liquid crystalline phase. Suitable organic dispersion stabilizers for the instant invention are well know in the art and include, but are not limited to any of several types of long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof.

Another example of organic dispersion stabilizer are alkanolamides having from about 14 to about 22 carbon atoms. Preferred alkanolamides are stearic monoethanolamide, stearic diethanolamide stearic monoisopropanolamide, stearic monoethanolamide stearate and mixtures thereof.

Still another class of useful dispersion stabilizer is long chain fatty acid esters such as stearyl stearate, stearyl palmitate, palmityl palmitate, trihydroxystearylglycerol and tristearylglycerol.

Another type of organic dispersion stabilizer is the so-called emulsifying waxes such as mixtures of cetostearyl alcohol with polysorbate 60, cetomacriogol 1000, cetrimide; a mixture of glycerol monostearate with a stearic soap, and partially neutralized stearic acid (to form a stearate gel).

Still another example of a suitable dispersion stabilizing agent is long chain amine oxides having from about 14 to about 22 carbon atoms. Preferred amine oxides are hexadecyldimethylamine oxide and octadecyldimethylamide oxide.

Example of a suitable polymeric dispersion stabilizing agents useful in the present invention include: carbohydrate gums such as cellulose gum, microcrystalline cellulose, cellulose gel, hydroxyethyl cellulose, hydroxypropyl cellulose, sodium carboxymethylcellu lose, hydroxymethyl carboxymethyl cellulose, carrageenan, hydroxymethyl carboxypropyl cellulose, methyl cellulose, ethyl cellulose, guar gum (including cationic guar gums such as Jaguar®), gum karaya, gum tragacanth, gum arabic, gum acacia, gum agar, xanthan gum and mixtures thereof. Preferred carbohydrate gums are the cellulose gums and xanthan gum.

An especially preferred type of polymeric dispersion stabilizer agent include acrylate containing homo and copolymers. Examples include the crosslinked poly acrylates sold by B.F. Goodrich under the CARBOPOL trade name; the hydrophobically modified cross linked polyacrylates sold by B.F. Goodrich under the PEMULEN trade name; and the alkali swellable acrylic latex polymers sold by Rohm and Haas under the ARYSOL or ACULYN trade names.

The above dispersion stabilizers can be used alone or in mixtures and may be present in an amount from about 0.1 wt. % to about 10 wt. % of the composition.

Other Ingredients

Perfume, which may be the combination of several fragrances, may be selected on the basis of the ability of the fragrances to be incorporated into the benefit agent delivery vehicle to provide enhanced fragrance delivery/benefit(s). However, as noted, perfume may also comprise a separate benefit agent which may be entrapped in a network formed by different structured benefit agent or may be added separately to the composition and not as part of the premix.

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and Vitamin A, C & E or their derivatives may be used advantageously in amounts of about 0.01% or higher if appropriate.

Polyethylene glycols which may be used include:

| Polyox | WSR-205 | PEG 14M, |
|--------|---------|----------|
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, walnut sheets and apricot seeds Another preferred ingredient is a crystallization suppressant or control agent which is used to suppress individual or mixtures of sunscreen ingredients from crystallizing out of solution. This may lead to reduced deposition. These suppression agents include, for example, organic esters such as $C_{10}$-$C_{24}$, preferably $C_{12}$-$C_{15}$ alkyl benzoate among others. Other examples include Bernel PCM from Bernel, and Elefac 205 from Bernel. Specific sunscreen(s) are more resistant to crystallization than others, e.g., butyl octyl salicylate.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight. Further, all ranges are to be understood to encompass both the ends of the ranges plus all numbers subsumed within the ranges.

EXAMPLES

Protocol

Ingredients Used

Sodium lauryl ether sulfate (SLES) was Steol CS330 from Stepan Co. (Northfield, Ill.). Cocamidopropyl betaine (CAPB) was Tego Betaine F50 from Goldschmidt Chemical Corp. (Hopewell, Va.). Refined sunflower seed oil was supplied by Welch, Holme and Clark Co., Inc. (Newark, N.J.). The petrolatum was white petrolatum from Penreco (Karns City, Pa.). The hydrogenated oils are commercially available from many manufacturers and were directly added to the formulations without further modification. Hydrogenated coconut, palm kernel, rapeseed and vegetable oils were supplied by Jarchem Industries, Inc. (Newark, N.J.). Castorwax was supplied by CasChem, Inc. (Bayonne, N.J.) Hydrogenated cotton seed oil, Stearine 07 supplied by Loders Croklaan. The commercially available AquaPel 15L from Exxon-Mobil Chemical (Edison, N.J.) is a linear butadiene-isoprene copolymer ($M_w$ 15,000).

Other materials used in the production of example bar formulations were as follows: propylene glycol supplied by Ruger Chemical Company; Pricerine 4911 palmitic-stearic acid supplied by Uniqema; sodium cocoyl isethionate and 82/18 soap supplied by Lever; Mackam 1L supplied by McIntyre Group Ltd.; Emery 916 glycerine supplied by Cognis Corporation; Superhartolan by Croda; and polyethylene glycols from the Pluracol series supplied by BASF.

Non-Bar Skin Cleanser Base

| Component | % wt. |
| --- | --- |
| Sodium Laureth Sulphate | 13.0 |
| Cocamidopropyl Betaine | 7.0 |
| Di Water | To 100.0 |
| Ph = 6.0-7.0 | |

Equipment Processing

Small batches of liquid cleanser prototypes were mixed using an overhead stirrer equipped with a high-efficiency paddle. Formulations were prepared in 250 ml stainless steel beakers which were placed in a thermally-controlled water bath (±1.0° C.).

Preparation of Structured Benefit Agent

Structured (e.g., hydrogenated oil structured) benefit agent premixes (delivery vehicles) were prepared at temperatures at or just above the melting points of the structurant or other mixtures of benefit agent structuring component. Typically, the structuring material was weighed into a 125 ml stainless steel beaker and then the appropriate amount of benefit agent (e.g., sunflower seed oil) was added based on the formulation specifications. The components were then heated by placing the beaker in a thermally-controlled water bath to melt the structuring material (e.g., wax or hydrogenated oil). The molten structured oil was stirred with a sigma blade mixer until uniformly mixed and, for liquid compositions, maintained at the elevated temperature until use (usually no more than 5 min). For bar compositions, the mixture was then either maintained at elevated temperature until its incorporation into a base formulation (i.e. a mixture of surfactants and bar structuring aids), or was allowed to cool to ambient temperature for incorporation into a bar base formulation. Optical modifiers were added with the molten structured oil prior to dispersion of the structured oil with the surfactant phase.

Preparation of Liquid Prototype Samples

Liquid cleanser formulations were prepared under similar processing conditions except for differences in mixing temperatures as necessary due to the varying melting temperatures of the structurants. Formulations were prepared in 250 ml stainless steel beakers immersed in a thermally-controlled water bath. First the SLES and CAPB along with additional water were added together and mixed at 100 to 150 rpm for 5 min using an overhead stirrer. Mixing was continued until homogeneous while the temperature was raised to that of the wax-oil premix. Just prior to addition of the oil phase, the mixing speed was increased to 250 rpm. The molten structured oil premix was then poured into the stirring surfactant mixture and stirred (about 20 minutes) while maintaining the elevated temperature. When mixing was completed, the finished product was removed from the temperature bath and allowed to cool to room temperature without further stirring. In the examples, component amounts are given as a weight percentage of the composition.

Preparation of Bar Prototypes.

Bars produced via a melt cast process route were made in Pyrex mixing vessels heated with electric heating mantles. Multiple turbine blades controlled with adjustable speed electric motors provided agitation for the vessel. Formulations were manually poured into polypropylene molds for cooling and solidification.

The base bar compositions were prepared by melting the bar structuring aids followed by addition of surfactants and then any additional components of the base formulation as required.

Bars produced via an extrusion process were mixed in a Patterson sigma blade mixer. The base bar carrying compositions were prepared by mixing components in the order described for the cast-melt process above.

The compositions were then passed over a chill roll set at 15° C. The flakes from the chill roll were then extruded through a Weber Seelander laboratory scale plodder. Bars were stamped on a Sigma Engineering air-driven press.

Silicone Rubber Surface Preparation (Silflo)

Silflo silicone rubber material (Flexico Developments, England) was used as received. Silflo replica surfaces for deposition trials were prepared with surface roughness to approximate the skin surface roughness. About 5 ml of Silflo material was squeezed from the stock bottle onto wax paper. After the addition of 2-3 drops of catalyst (supplied with the Silflo) the liquid material will thicken while mixing with a stainless steel spatula (about 30 seconds). A piece of 100 grit sandpaper was cut to 4×4 cm square and taped to a surface to leave approximately 2.5×2.5 cm exposed. The thickened material was spread evenly over the sandpaper and allowed to dry (about 10 min). Once set, the solid Silflo replica was separated by peeling away the sandpaper and covering the exposed adhesive side of the tape with new pieces of tape. The replica surface was a negative of the sandpaper surface and thus is textured. The 100 grit was chosen to approximate the surface roughness of skin.

Shine Enhancement Quantification Test

Each corner of the 7 $cm^2$ squares on the volar area of forearm were marked with a marker. This area is flat and has even texture, so variation caused by skin stretching was minimized. Baseline images were taken before the product application. After obtaining the baseline images, faucet water was set up to 60 ml per minute. Then 21 μL of a shower gel was pipetted to a testing site. Sample was rubbed for about 15 seconds with a finger-cot, 15 seconds was allowed for waiting and then area was rinsed for 15 seconds. These steps were repeated until all testing sites were finished. There was a 15 minute wait, and three images of each testing site were taken for shine enhancement. All products were tested on three subjects and results were averaged.

A Charm-view Microscope was used with a 30× magnification lens under parallel-polarized condition. PhotoSuite III was used to capture images in Bitmap format. A program in IDL was developed to process the captured images and list results in a text file. Average shine intensity for the brightest 30720 pixels was calculated as the shine intensity. Enhancement of skin shine is defined by the difference in shine intensity after product application over the baseline.

Sunflower Seed Oil Deposition Protocol for Liquid Compositions

The amount of sunflower seed oil that deposits from the structured oil formulations was assessed on the Silflo replica surfaces. Newly prepared samples of formulations were tested in triplicate by applying product to the Silflo surface, rubbing in the product, rinsing and then extracting any oil remaining bound to the surface. In practice, 8.6 mg of product was applied per square centimeter of surface. After addition of one drop of tap water, the product was rubbed on the surface with one finger for 15 seconds (approximately 20 circular rubs). The surface was then rinsed with tap water maintained at 37° C. and a flow rate of 13-14 ml/sec, holding the sample 5 cm away from the tap at an angle of 450. After rinse, the sample was blotted once with a towel and allowed to air dry for 15 min. The Silflo replica was then cut from the tape border with a razor blade and placed into a 20 ml glass vial with 10 g of hexanes. After mixing with an automatic "wrist action" shaker for 15 min, the Silflo replica was removed from the vial. For analysis of oil content, the extraction solvent was transferred to 1 ml glass vials.

Sunflower Seed Oil Deposition Protocol for Bar Compositions

Full thickness porcine skin was obtained from Sinclair Research Center, Inc. It was cut into pieces of size 8 cm×10 cm. The skin was shaved with a disposable razor, rinsed with warm water and then rinsed with ethyl alcohol (10 ml) and wiped dry with an absorbent paper towel. After cleaning in this manner, the skin was then hydrated for 10 seconds under running tap water set to 100° F. The amount of bar product applied to the skin was 3.3 mg/$cm^2$. Thus, the appropriate amount of bar material was weighed out according to the area of skin to be washed and then an equal amount of water was added to the bar sample and this was then allowed to sit for 15 min at ambient temperature in a covered vessel. The slurry so formed was then transferred onto the piece of skin to be washed and spread evenly over the entire surface using one hand covered with a textured latex glove. The skin was then washed over its entire area using the gloved hand, rubbing in a circular motion for 30 s. The skin was then rinsed under a tap for 10 seconds at a flow rate of 70 ml/minute and temperature of 100° F. Excess water was removed by patting the skin with a paper towel. The skin was then allowed to air dry at ambient temperature for 15 minutes. The sunflower seed oil that was deposited on the skin during the wash procedure was recovered by solvent extraction. A glass cylinder (7 $cm^2$ area) was firmly placed onto the skin surface and 2 ml of solvent (25:75 (v/v) chloroform:methanol) dispensed into the cylinder and stirred with a glass rod for 1 minute. The solvent was then transferred to a 10 ml vial using a disposable plastic pipette. The extraction process was repeated two more times and all three portions of the solvent were combined in the single vial. The sample was then filtered using a disposable syringe fitted with a 0.45 μm Millipore disposable filter. The solvent was evaporated under nitrogen.

Sunflower Seed Oil Deposition Analysis by Thin Layer Chromatography (TLC) for Liquid Compositions Analysis of oil concentration in the hexanes extracts was performed using thin layer chromatography (TLC). Samples were spotted onto TLC plates using an automatic TLC spotter (CAMAG Automatic TLC Sampler 4, CAMAG, Switzerland). Along with the sample extracts, six standard solutions of sunflower seed oil in hexanes were also spotted on each plate. Standards were prepared at concentrations ranging from 125 to 450 μg/g. TLC plates were cleaned before use by soaking first in methanol and then isopropanol for 15 min each and then dried overnight. After spotting, plates were placed in a glass TLC chamber containing 100 ml of developing solution (70% hexane, 29% ethyl ether, 1% acetic acid). When the solution had traveled ¾ of the plate height, the plate was removed and air dried overnight. After drying, the TLC plates were immersed in staining solution (aqueous solution containing 10% cupric sulfate, 8% phosphoric acid). After blotting excess staining solution from the plates, they were heated for 30 min on a hotplate set at 165° C. For measurement of the deposited oil, the stained plates, now having charred spots representing the deposited oil extracted from the Silflo surfaces, were digitally scanned using a GS-700 Imaging Densitometer (Bio-Rad Laboratories, Hercules, Calif.). Using the scanning software, the intensity of the sample spots was calculated based on a standard curve generated for the 6 standards applied to the plate. From these apparent intensity values, the concentration of sunflower oil in the extracts was calculated.

Sunflower Seed Oil Deposition Analysis by High Performance Liquid Chromatography (HPLC)

Quantification of the sunflower seed oil recovered from the deposition trials was via high performance liquid chromatography. Following evaporation of the solvent under nitrogen as described above, the sample was reconstituted in mobile phase solvent (70:30 (v/v) acetone:acetonitrile). LC separation was performed on a Hewlett-Packard Series 1100 HPLC. Detection was via a light-scattering detector, Alltech ELSD 2000. The column used for LC separation was a Waters Symmetry $C_{18}$ (39×150 mm) kept at 30° C. The mobile phase was 70:30 (v/v) acetone:acetonitrile. The flow rate was 0.8 ml/min. The sample injection volume was 100 µl. Run time was 18 min. Detector nitrogen flow rate was 0.9 L/min and evaporative tube temperature was 40° C. (with impactor OFF). The elution time for the peak of interest was about 6.2 min.

Standards were prepared at concentrations ranging from 10 to 40 ppm of sunflower seed oil. The level of sunflower oil in the extracts was calculated based on the standard curve generated from the standard solutions.

Droplet Size Measurement

Droplet size was measured from images captured of the oil droplets in the formulations. Microscopic images were taken from samples of the body wash prototypes by placing a small amount (<0.1 ml) onto a glass slide. The sample was gently spread on the slide following placement of a cover slip. Samples were examined at 100× magnification using an optical microscope (Axioplan Model, Carl Zeiss, Inc., Thornwood, N.Y.). The microscope was equipped with a video camera, image processor and video monitor. The camera was connected to a personal computer and images were digitally captured using appropriate software. Using the imaging software, (structured) oil droplets were measured individually. At least 200 droplets were measured for each formulation sample.

Viscosity Shear Profile Measurement

The Rheometric Scientific ARES controlled strain rheometer (SR-5, RheometricScientific, Piscataway, N.J.) was used to determine shear profiles of structured benefit agents used herein. The rheometer was set up with parallel plates 25 mm in diameter typically with 200 to 500 µm gaps between the top and bottom plates. Test temperature was 37° C. Programmed steady shear rate sweeps were performed where the shear rates were logarithmically varied from 0.1 to 1000 seconds$^{-1}$, with 5 points recorded per decade. The shear scan typically takes 5 minutes to complete. The output is viscosity as a function of shear rate.

Yield Stress Measurement

The yield stress values of the structured benefit agents were measured using a Rheometric Scientific Stress Controlled Rheometer model SR-5 (Rheometric Scientific, Piscataway, N.J.). Stress ramp tests were performed on samples in stress ranges from 0.2 to 12000 Pa using either a 25 mm or 40 mm cone and plate fixture. Samples of the structured benefit agent to be tested were loaded between the fixture (top plate) and bottom plate. Using the RSI Orchestrator software supplied with the instrument, tests were conducted by incrementing the applied stress from 0.2 Pa to user defined final stress value. The user also sets testing time typically at 15 minutes. Tests are completed when the sample yields (flows), which is noted by a sharp decrease in sample viscosity as observed as the software plots the experimental data as the test is conducted. Yield stress values were determined from linear plots of the viscosity versus strain. The first data point after the peak of the curve is the yield value. Alternatively, lines can be fit to the linear portions of the curve before and after the peak. The intersection of the line will give the yield value. Yield stress can also be determined from semi-logarithmic plots of the viscosity (Pa-s) against stress (Pa). The yield value is the first data point for stress after the linear portion of the curve at lower stress values. The yield stress values here are to be understood as a critical yield stress value or the value of the stress where the material begins to flow.

Examples 1 and 2 and Comparatives A to C

This example is to highlight the advantage of structuring the benefit agent and of the order of addition of structurant and benefit agent.

Shower formulations were prepared having various compositions. A liquid cleanser composition without benefit agent (sunflower seed oil) being structured (Comparative A) was prepared at room temperature by mixing 20% w/w of sunflower seed oil with 80% aqueous surfactant phase (comprising water and surfactants) using an overhead mechanical mixer equipped with a high efficiency stirrer and stirring at 250 rpm.

Comparative A composition is set forth below:

Comparative A

Control, Skin Cleanser Base

| Component | % wt. |
|---|---|
| Sodium Laureth Sulphate | 13.0 |
| Cocamidopropyl Betaine | 7.0 |
| Sunflower Seed Oil (unstructured) | 20.0 |
| Di Water | To 100.0 |
| Ph = 6.0-7.0 | |

Examples 1 and 2 were prepared by mixing 25% w/w of a structured oil (comprising 5% w/w of a structurant such as petrolatum or ultraflex or amber wax; and 20% w/w sunflower seed oil) to the aqueous surfactant phase. For these formulations, the structured oil was prepared by addition of the structurant to the sunflower seed oil, heating the mixture to a temperature above the melting point of the structurant and mixing until uniform. The molten structured oil was only then combined with (e.g., added to) the aqueous surfactant phase which was maintained at the same temperature as the structured oil. After mixing for 15 minutes, the formulation was cooled to room temperature. The structurant must be, and was, added to the oil phase prior to dispersion of the structured oil phase into the aqueous surfactant phase.

An example of the composition of the invention is set forth below as Example 1.

Example 1

Invention, Cleanser+5% Petrolatum

| Composition | % Wt. |
|---|---|
| Sodium Laureth Sulphate | 13.0 |
| Cocamidopropyl Betaine | 7.0 |
| Petrolatum (Structurant) | 5.0 |
| Sunflower Seed Oil | 20.0 |
| Di Water | To 100.0 |

Example 2 (Invention, Cleanser+5% microcrystalline wax) was prepared in the same way as Example 1 except the structurant was microcrystalline wax. That is, the example comprises the same formulation as Example 1, except 5.0% petrolatum is replaced by 5.0% Ultraflex® amber wax.

Comparative B (Comparative, Cleanser+5% petrolatum) comprises the same formulation as Example 1, including use of 5% petrolatum structurant. It differs from Example 1 only in that the 5% petrolatum and the sunflower seed oil were added separately to the surfactants.

Comparative C (Comparative, Cleanser+5% microcrystalline wax) comprises the same formulation as Example 2 and differs only in that the 5 wt. % ultraflex amber wax and sunflower seed oil were added separately to the surfactants.

Table 1 below sets forth the deposition results for each of the compositions:

Sunflower Seed Oil Deposition from Liquid Cleanser Formulations with Structured Oils

TABLE 1

| Formulation | Deposition, $\mu g/cm^2$ |
|---|---|
| Comparative A (no structurant) | 0 |
| Example 1 | 158 |
| Comparative B (separate addition of oil and structurant) | 34 |
| Example 2 | 980 |
| Comparative C (separate addition) | 49 |

As seen from Table 1, the importance of the order of addition of the components to create the structured oil is demonstrated by comparing oil deposition from Examples 1 and 2 with formulations prepared from the same components but differing processing conditions. Comparatives B and C were prepared by the separate addition of structurant and sunflower seed oil to the aqueous surfactant phase. For these formulations, 5% w/w of structurant, 20% w/w sunflower seed oil and 75% of aqueous surfactant phase were heated in separate vessels to the same temperature which is above the melting point of the structurant. The sunflower seed oil was added to the aqueous surfactant phase and mixed with an overhead stirrer as described above. The structurant was then added separately to the mixture and the entire formulation was mixed for 15 minutes. After mixing, the formulation was cooled to room temperature.

As seen clearly, Comparative B & C (separate addition) have far less deposition.

Example 3 to 5 and Comparative D

A liquid cleanser with the composition shown in Comparative A plus the addition of an oil phase structurant was used to prepare Examples 3-5 and Comparative D Example 3 (Invention, Cleanser+5% paraffin wax) comprises the same formulation as Example 1 except that it uses 5% paraffin wax as structurant instead of 5% petrolatum. It is prepared as per the invention, i.e., structurant and oil mixed before addition to surfactant phase.

Example 4 (Invention, Cleanser+5% animal wax) comprises same formulation as Example 1 except that it uses 5 wt. % beeswax as structurant instead of 5% by wt. petrolatum. Again, structurant and oil are combined before combining with surfactant phase.

Example 5 (Invention, Cleanser+2.5% petrolatum+2.5% microcrystalline wax) comprise same formulation as Example 1 except it uses 2.5 wt. % petrolatum and 2.5 wt. % ultraflex amber wax (microcrystalline wax) instead of 5% by wt. petrolatum. Again structurant and oil are combined separately from combination with surfactant phase.

The following comparative was also prepared.

Comparative D

Comparative, Cleanser+10% Polymer Thickener, which is AquaPel 15, a Linear Copolymer of Butadiene/Isoprene

| Component | % Wt. |
|---|---|
| Sodium Laureth Sulphate | 13.0 |
| Cocamidopropyl Betaine | 7.0 |
| AquaPel 15L (copolymer of butadiene/isoprene) | 10.0 |
| Sunflower Seed Oil | 15.0 |
| Di Water | To 100.0 |

Sunflower Seed Oil Deposition from Liquid Cleanser Formulations with Structured Oils

TABLE 2

| Formulation | Deposition, $\mu g/cm^2$ |
|---|---|
| Comparative A (Sunflower Oil only)* | 0 |
| Example 2 (ultraflex amber wax)* | 980 |
| Example 3 (paraffin wax) | 649 |
| Example 4 (beeswax) | 245 |
| Example 5 (petrolatum + ultraflex wax) | 865 |
| Comparative D (AquaPel 15L) | 51 |

*From previous Table 1
As seen only crystalline wax structurants (2-5) yield sunflower seed oil deposition of 60 $\mu g/cm^2$ or greater. Comparative D, a non crystalline material, fails to yield these results.

Examples 6-10

In order to show that structuring works with a variety of crystalline waxes (at droplet sizes averaging 4.9-6.2 μm diameter) applicants prepared the following liquid cleanser examples in accordance with the process if the invention (i.e., benefit agent sunflower seed oil and structurant were first combined)

Example 6

Invention, Cleanser+5% Microcrystalline Wax 95 wt % liquid cleanser of Comparative A
5 wt. % Victory amber wax Example 7

Invention, Cleanser+5% Microcrystalline Wax 95 wt % liquid cleanser of Comparative A
5 wt. % Multiwax ML-445

Example 8

Invention, Cleanser+5% Microcrystalline Wax 95 wt % liquid cleanser of Comparative A
5 wt. % Multiwax 180-M

Example 9

Invention, Cleanser+5% Microcrystalline Wax 95 wt % liquid cleanser of Comparative A
5 wt. % Multiwax W-835

Example 10

Invention, Cleanser+2.5% Microcrystalline Wax 97.5 wt % liquid cleanser of Comparative A
2.5 wt. % Mekon White Structured benefit agent droplet size and deposition results are set forth in Table 3 below:

Sunflower Seed Oil Deposition from Liquid Cleanser Formulations with Structured Oils

TABLE 3

| Formulation | Average Droplet Diameter, μm | Deposition, μg/cm$^2$ |
|---|---|---|
| Example 6 (Victory amber wax) | 6.2 | 876 |
| Example 7 (Multiwax ML-445) | 6.2 | 852 |
| Example 8 (Multiwax 180-M) | 4.9 | 893 |
| Example 9 (MultiwaxW-835) | 5.9 | 793 |
| Example 10 (Mekong White) | 4.9 | 309 |

As seen from Table 3, deposition was excellent over wide range of waxes, and with average droplet sizes much lower than that suggested for best deposition of hydrophobic benefit agent by U.S. Pat. No. 6,066,608, which suggests that droplets have average diameter larger than 200 μm; U.S. Pat. No. 5,854,293, which suggests droplets larger than 500 μm, or U.S. Pat. No. 5,661,189, which suggests droplets from 50-500 μm.

Examples 11-19

In order to show that benefit agent oils can be structured using varying amounts of structurants (e.g., 0.5% to 16.0%) and that the level of deposition can be manipulated by the amount of structurant, applicants prepared the following examples

Example 11

Invention, Cleanser+0.5% Microcrystalline Wax 99.5 wt % liquid cleanser of Comparative A
0.5 wt. % Ultraflex amber wax

Example 12

Invention, Cleanser+1.0% Microcrystalline Wax 99.0 wt % liquid cleanser of Comparative A
1.0 wt. % Ultraflex amber wax

Example 13

Invention, Cleanser+2.0% Microcrystalline Wax 98.0 wt % liquid cleanser of Comparative A
2.0 wt. % Ultraflex amber wax

Example 14

Invention, Cleanser+4.0% Microcrystalline Wax 96.0 wt % liquid cleanser of Comparative A
4.0 wt. % Ultraflex amber wax

Example 15

Invention, Cleanser+2.0% Microcrystalline Wax 94.0 wt % liquid cleanser of Comparative A
6.0 wt. % Ultraflex amber wax

Example 16

Invention, Cleanser+8.0% Microcrystalline Wax 92.0 wt % liquid cleanser of Comparative A
8.0 wt. % Ultraflex amber wax

Example 17

Invention, Cleanser+10.0% Microcrystalline Wax 90.0 wt % liquid cleanser of Comparative A
10.0 wt. % Ultraflex amber wax

Example 18

Invention, Cleanser+12.0% Microcrystalline Wax 88.0 wt % liquid cleanser of Comparative A
12.0 wt. % Ultraflex amber wax

Example 19

Invention, Cleanser+16.0% Microcrystalline Wax 84.0 wt % liquid cleanser of Comparative A
16.0 wt. % Ultraflex amber wax Deposition results for the various compositions are set forth below:

Sunflower Seed Oil Deposition from Liquid Cleanser Formulations with Structured Oils

TABLE 5

| Example | Deposition, μg/cm$^2$ |
|---|---|
| 11 (0.5% ultraflex amber wax) | 65 |
| 12 (1% ultraflex amber wax) | 213 |
| 13 (2% ultraflex amber wax) | 320 |
| 14 (4% ultraflex amber wax) | 727 |
| 2 (ultraflex amber wax) | 980 |
| 15 (6% ultraflex amber wax | 1022 |
| 16 (8% ultraftex amber wax) | 1178 |
| 17 (10% ultraflex amber wax) | 1328 |
| 18 (12% ultraflex amber wax) | 1080 |
| 19 (16% ultraflex amber wax) | 1076 |

As seen from Table 5, small or large amounts of structurant can be used. The level of structurant can be used to control deposition (e.g., increasing the amount of structurant can increase the level of deposition as seen, for example, in Table 5).

The wax content is measured as percent of overall composition. That is, for example, Example 12 combines 1% microcrystalline wax with 20% sunflower seed oil in a premix which, when in molten state, is then combinable with the rest of the composition (of Comparative A).

Examples 20-21, Comparative E

In order to show that deposition will occur with or without use of deposition aid (i.e., cationic polymer), applicants made the following examples:

Example 20

Invention, Cleanser+5.0% Microcrystalline Wax+1.0% Polymer Stabilizer 94 wt % liquid cleanser of Comparative A
5 wt. % Ultraflex amber wax
1 wt. % Jaguar polymer

Example 21

Invention, Cleanser+5.0% Microcrystalline Wax+1.0% Polymer Stabilizer 94 wt % liquid cleanser of Comparative A
5 wt. % Victory amber wax
1 wt. % Jaguar polymer

Comparative E

Cleanser+1.0% Polymer Stabilizer 99 wt % liquid cleanser of Comparative A
1 wt. % Jaguar polymer
Results of deposition are set forth in Table 6 below:

Sunflower Seed Oil Deposition from Liquid Cleanser Formulations with Structured Oils

TABLE 6

| Example | Deposition, µg/cm² |
|---|---|
| Example 2 (5% ultraflex amber wax)* | 980 |
| Example 20 (5% ultraflex amber wax, 1% JaguarC13s) | 473 |
| Example 6 (5% Victory Amber Wax)** | 876 |
| Example 21 (5% victory amber wax, 1% Jaguar C13s) | 388 |
| Comparative A (no benefit agent structurant) | 0 |
| Comparative E (no benefit agent structurant, 1% Jaguar C13s) | 44 |

*From Table 1
**From Table 3

As seen from results in Table 6, deposition occurs even without use of cationic polymer deposition aid.

Examples 22 and 23 and Comparatives F-H

Five body wash formulations were prepared as described in the protocol section using formulations shown in Table 7 below. Coated mica was added to molten sunflower seed oil: wax premix and then added to the surfactant phase.

TABLE 7

Formulation for shine enhancement study.

| Material | Example 22 | Comparative F (No optical modifier) | Example 23 | Comparative G (No optical modifier) | Comparative H (No structured oil) |
|---|---|---|---|---|---|
| Alkyl Amphoacetate | 2.9 | 2.9 | 2.9 | 2.9 | 2.9 |
| Steol CS230 (SLES-2EO) | 5.7 | 5.7 | 5.7 | 5.7 | 5.7 |
| Capric Acid | 1.1 | 1.1 | 1.1 | 1.1 | 1.1 |
| Lauric Acid | 1.1 | 1.1 | 1.1 | 1.1 | 1.1 |
| Glycerin | 3.5 | 3.5 | 3.5 | 3.5 | 3.5 |
| Cationic Polymer (i.e., Jaguar C13S) | 0.5 | 0.5 | 0.5 | 0.5 | 0.5 |
| Sunflower Seed Oil: Victory Amber Wax (4:1) | 20 | 20 | 9.6 | 9.6 | 0 |
| Coated Mica | 5 | 0 | 2.4 | 0 | 2.4 |
| Water | | | Add to 100 | | |

The shine enhancement of these samples are shown in Table 8. Shine enhancement was measured instrumentally using the shine enhancement test on skin. It can be seen that without the mica (Comparative F & G), formulation will not show shine enhancement benefit. Without the wax structured oil (Comparative H), formulation can not provide shine enhancement either. When oil was used as carrier for an optical active such as coated mica, significant shine enhancement can be achieved (Examples 22 and 23).

TABLE 8

Shine Enhancement of Examples 22 and 23 and Comparatives F–H

| | Sample | | | | |
|---|---|---|---|---|---|
| | Example 22 | Comparative F | Example 23 | Example G | Comparative H |
| Shine enhancement | 17.9 | −2.6 | 7.3 | −2.6 | −1.1 |

The invention claimed is:

1. Personal product liquid composition comprising:
   (1) 1 to 75% by wt. (weight) of a surfactant material selected from the group consisting of anionic, nonionic, amphoteric, cationic surfactants and mixtures thereof wherein at least 1% by wt. of said composition comprises anionic surfactant;
   (2) 0.1 to 90% of a structured benefit agent droplet composition comprising:
      (a) 50 to 99.9% by wt. of structured benefit agent composition wherein said benefit agent comprises sunflower seed oil; and
      (b) 50 to 0.1% structured benefit agent structuring material made from crystals and selected from the group consisting of crystalline structurant selected from the group consisting of natural or synthetic crystalline waxes, natural or synthetic hydrogenated oils or fats, fatty acids, fatty alcohols, salts of fatty acids, hydroxy fatty acids, fatty acid esters and mixtures thereof; and
   (3) optical modifier or modifiers,
   wherein droplet diameter of structured benefit agent is in range of 1-15 µm;
      wherein the crystals in said structuring material have an aspect ratio defined by A/B>1, the length A being understood as the longer of the two dimensions when considering length and width, B;
      wherein, structurant of 2(b), benefit agent of 2(a) and optical modifier of (3) are heated to molten state and mixed and are then separately combined with a surfactant containing composition and cooled to room temperature, and there is provided enhanced benefit of the optical modifier of at least 5% relative to the effect provided by the same optical modifier in the absence of structured benefit agent in the final composition.

2. A composition according to claim 1, wherein said natural crystalline wax is selected from the group consisting of mineral waxes, petroleum based waxes, plant or vegetable waxes and animal waxes.

3. A composition according to claim 2, wherein said petroleum based wax is paraffin or microcrystalline wax.

4. A composition according to claim 1, wherein said synthetic crystalline wax is polyethylene, a polymethylene, a chemically modified wax, polymerized a-olefins and synthetic animal waxes.

5. A composition according to claim 1, wherein said benefit agent is a droplet having a weight average diameter less than 500 µm.

6. A composition according to claim 1, wherein the enhanced benefit of the optical modifier is shine and there is enhanced shine benefit of at least 5 intensity units.

7. A method of enhancing visual appearance of skin comprising applying to skin or other substrate a personal product composition comprising:
   (1) 1 to 75% by wt. (weight) surfactant wherein at least by wt. of the composition is anionic surfactant; and
   (2) 0.1 to 90% of a benefit agent vehicle;
      (a) 50 to 99.9% by wt. of structured benefit agent composition wherein said benefit agent comprises sunflower seed oil and wherein said benefit agent further comprises an optical modifying agent or component
      (b) 50 to 0.1% structuring material made from crystals and selected from the group consisting of crystalline structurant selected from the group consisting of natural or synthetic crystalline waxes, natural or synthetic hydrogenated oils or fats, fatty acids, fatty alcohols, salts of fatty acids, hydroxy fatty acids, fatty acid esters and mixtures thereof; and
   (3) optical modifier or modifiers,
      wherein the crystal crystals in said structuring material have an aspect ratio defined by A/B>1, length A being understood as the longer of the two dimensions when considering length and width, B;
      wherein, structurant of 2(b), benefit agent of 2(a) and optical modifier of (3) are heated to a molten state and mixed, then separately combined with a surfactant containing composition and there is provided enhanced benefit of the optical modifier of at least 5% relative to the effect provided by the same optical modifier in the absence of structured benefit agent in the final composition.

* * * * *